United States Patent [19]

Sato

[11] Patent Number: 4,691,693
[45] Date of Patent: Sep. 8, 1987

[54] MASSAGE DEVICE

[75] Inventor: Ray S. Sato, Carson, Calif.

[73] Assignee: Magnetic Massage Company, Los Angeles, Calif.

[21] Appl. No.: 902,462

[22] Filed: Sep. 2, 1986

[51] Int. Cl.$^4$ .............................................. A61H 7/00
[52] U.S. Cl. ...................................... 128/24.1; 128/67
[58] Field of Search .................... 128/24.1, 24.2, 24.3, 128/24.4, 24.5, 62 R, 399, 44, 56, 61, 64, 67

[56] References Cited

U.S. PATENT DOCUMENTS

| 2,097,455 | 11/1937 | Fisher | 128/24.2 |
| 2,929,374 | 3/1960 | O'Gara | 128/24.1 |
| 2,985,166 | 5/1961 | Burkhardt | 128/24.1 |
| 3,489,138 | 1/1970 | Lifschitz | 128/24.2 |
| 3,503,395 | 3/1970 | Meyer | 128/24.2 |
| 4,632,095 | 12/1986 | Libin | 128/67 |

FOREIGN PATENT DOCUMENTS 115949 9/1979 Japan .................................. 128/24.1

Primary Examiner—Edgar S. Burr
Assistant Examiner—Huong Q. Pham
Attorney, Agent, or Firm—Beehler, Pavitt, Siegemund, Jagger, Martella & Dawes

[57] ABSTRACT

A hand-held pistol grip jacket holds an electric heater provided with a heat-absorbing core from which a threaded shaft projects outwardly beyond the jacket. One or more disc-like applicator assemblies are each provided with a metal mounting plate having a centrally located complementarily tapped recess for removably mounting the applicator assembly on the threaded shaft. Each applicator assembly comprises a doughnut-shaped permanent magnet anchored to the mounting plate. A smooth surfaced face plate covers the magnet and, with the aid of a finish plate, serves to engage the body of the subject being massaged.

13 Claims, 4 Drawing Figures

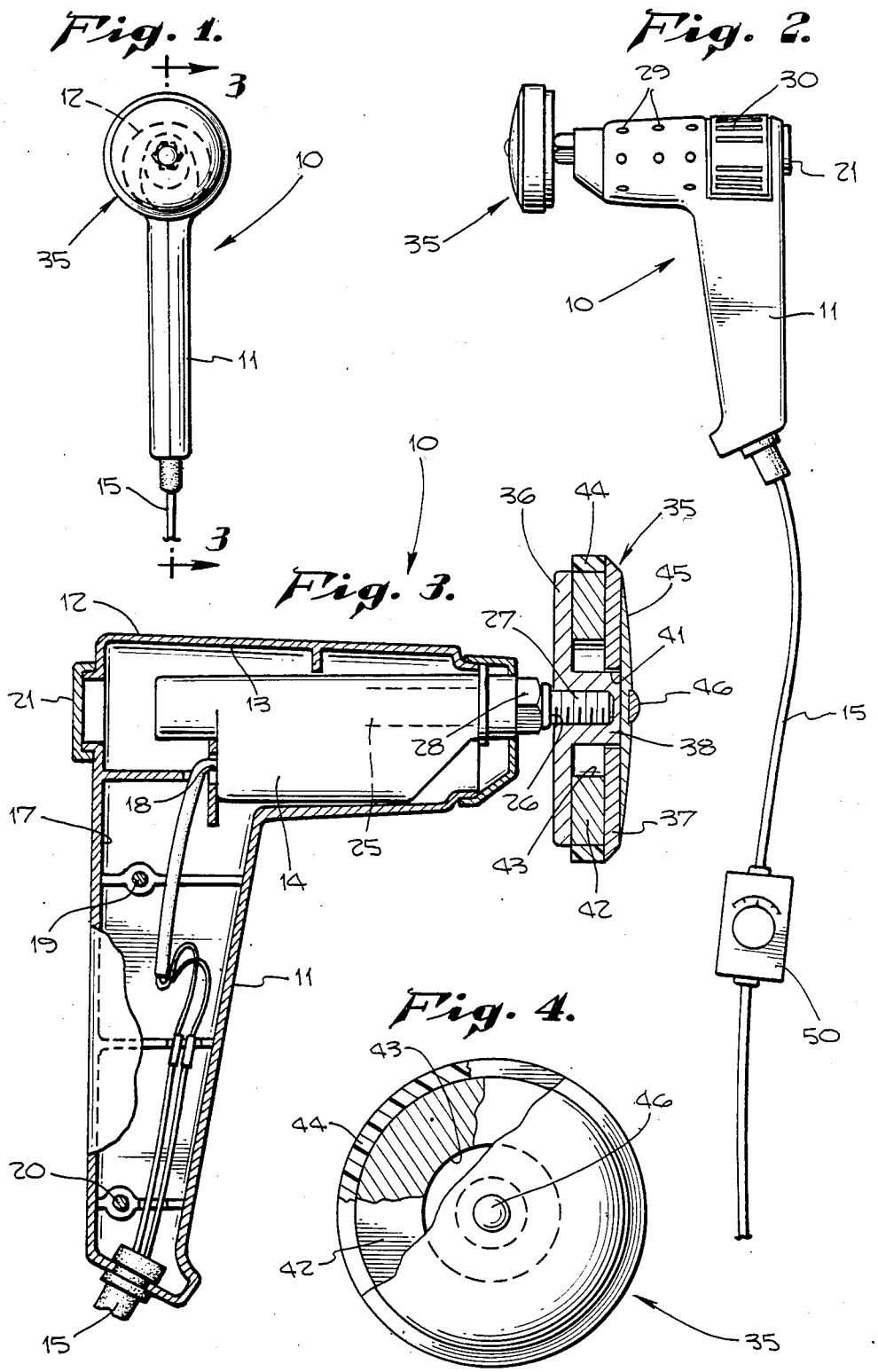

MASSAGE DEVICE

The invention herein disclosed concerns a heated handheld device for massaging parts of the human body to relieve stiffness, fatigue and pain and to enhance a general feeling of well-being.

Sensations of bodily stiffness, fatigue and pain, especially of the joints, has heretofore prompted the employment of a variety of devices for alleviation of such feeling. Among the more common of those devices has been hot pads, usually electrically heated. Although serving as a temporary relief, the structure of devices such as pads is one not readily capable of reaching depressions and deep-seated muscular locations where need for heat treatment may be greatest.

Resort has also been had to vibrators, some designed to be strapped to the hand of an operator, so that the operator's fingers may do the massaging. Comparable devices on other occasions are of a construction so that they can be reversed in position on the hand for direct application of a heated vibrating plate to the body. In either case, it is routinely difficult for the operator to massage the joints and areas of his own person. Other devices more structurely complicated have had a degree of acceptability, but lack the ability to be used readily by the person in need of treatment without some outside assistance.

It is therefore among the objects of the invention to provide a new and improved heated massaging device which an operator can readily use on parts of the body, including his own person, and which is capable of reaching deep-seated areas in and around the joints, for example, to provide a maximum amount of treatment.

Another object of the invention is to provide a new and improved heated massaging device of a shape and size to assist maximum amount of penetration of deep-seated muscular areas for massaging manipulation accompanied by the benefits of heat.

Another object of the invention is to provide a new and improved heated massaging device of a construction so that when held in the hand of the operator, whether for use on his own person or that of another, it is provided with a body-contacting applicator of a shape capable not only of massaging broad surfaces of the person, but also capable of being manipulated in and around the joints to maximize the effect.

A still further object of the invention is to provide a new and improved heated massaging device of a design and construction such that any one or another of an assortment or set of applicators may be applied at will, applicators being those of different construction and configuration to satisfy different massaging needs.

Still further among the objects of the invention is to provide a new and improved heated massaging device which operates in company with a strong magnetic field in order to enhance the effect of the heated massaging applicator of whatever type may be chosen, the source of magnetism also being one which can be subjected to a heated condition during operation.

With these and other objects in view, the invention consists of the construction, arrangements, and combination of the various parts of the device serving as an example only of one or more embodiments of the invention, whereby the objects contemplated are attained, as hereinafter disclosed in the specification and drawings and pointed out in the appended claims.

In the drawings:

FIG. 1 is a side elevational view of the massaging device in operating condition.

FIG. 2 is a front elevational view of the device of FIG. 1.

FIG. 3 is a longitudinal sectional view of the device on the line 3—3 of FIG. 2.

FIG. 4 is a forward end view of the applicator partially broken away to show the interior structure.

In an embodiment of the invention chosen for the purpose of illustration, there is shown a jacket, indicated generally by the reference character 10, which, for convenience, is provided with a pistol grip 11, at the free end of which is a barrel 12 havaing a chamber 13 for mounting and retention of an electric heater 14.

The heater is supplied with electrical energy by use of a conventional extension cord 15 which enters the hand-held end of the piston grip 11 at the end 16, passing through a chamber 17 to an inside end location 18 of the electric heater 14. Opposite half portions of the jacket 10 may be releasably anchored together by means of screws 19 and 20 and with the assistance of a closure ring 21.

The electric heater 14 as a part of its design and construction is provided with a core 25, suggested by the broken lines in FIG. 2, the core being adapted to absorb heat and pass it by conduction to an exposed shaft 26 which has a threaded end 27. A mounting nut 28 may be employed to stabilize the location of the shaft 26 with respect to the jacket 10. In that it is the expectation that heat will accumulate within the chamber 13, the surrounding wall of the barrel 12 is preferably provided with vent holes 29 and air circulating slots 30.

Of particular concern is the provision of one or more applicator assemblies 35. In the chosen embodiment the applicator assembly consists of a heat transfer plate 36 at the rear side and a face plate 37 on the forward side. The heat transfer plate 36 is built with a forwardly projecting boss 38 containing a central tapped bore 39 for coupling to the threaded end 27 of the core 25. In the chosen embodiment the boss 38 extends through a central hole 41 of the face plate 37. The heat transfer plate 36 and face plate 37 may, if preferred, be of paramagnetic material.

Separating the plates 36 and 37 is an annular permanent magnet 42, preferably magnetized to provide a magnetic field of maximum capacity. In the chosen embodiment there is a relatively large central opening 43 in the magnet which accommodates the boss 38, leaving an annular space surrounding the boss. Although there is a strong magnetic force holding the plates in position on opposite faces of the magnet, the plates are made non-removable by interposition of an adhesive to permanently fix all parts together. To further enhance the appearance and operability of the applicator assembly, there is an annular ring 44 around the exterior circumference of the permanent magnet 42, also attached by means of an adhesive.

Over the forward face of the face plate 37 may be provided a finish plafte 45 which may be of non-magnetic material, also fastened by means of an appropriate adhesive. The finish plate, as shown, covers a substantial portion of the face plate 37 and may, on occasions, be provided with a decorative central button 46. Edges of exposed portions of the plates 36 and 37 and the annular ring 44 are chamfered so that all exposed edges are contoured and smooth for application to body parts.

It is further of interest to note that the construction of the various parts of the applicator assembly calls for relatively heavy gauge material so that the weight of the applicator assembly is appreciably greater than the weight of the jacket 10 and its contents by a ratio of about two to one. It is further of consequence to note that the circumference of the applicator assembly is substantially greater than the thickness which produces a finish plate area relatively large for applications to flat portions of the body and a circumferential shape correspondingly small so that the edge of the applicator assembly can be worked in and around joints needing massaging and bodily recesses not readily reached by the flat finish plate. Additionally, the strength and location of the magnetic field is one wherein the magnetic force can most easily reach the portions of the body which are being heated and massaged.

A warm applicator assembly is preferable to an applicator assembly which is hot to the touch. Accordingly, a regulator 50 may be employed in the extension cord 15 to control the degree of heating. When the electric heater 14 is energized, the core 25 is heated and heat by conduction flows through the shaft 26 to the heat transfer plate 36 and from the plate 36 to both the magnet 42 and the face plate 37. The entire applicator assembly, accordingly, is heated and having, as it does, a realtively large mass, is capable of holding the heat for long enough periods to provide an acceptable massaging effect.

Although one applicator assembly 35 has been shown in detail, it should be appreciated that additional applicator assemblies, either smaller or larger in diameter, may be employed, weights may differ to a degree, and the applicator assembly not necessarily confined to the precise details and made non-circular in circumference.

While a particular embodiment of the present invention has been shown and described, it will be obvious to those skilled in the art that changes and modifications may be made without departing from the invention in its broader aspects and, therefore, the aims of its appended claims are to cover all such changes and modifications as fall within the true spirit and scope of this invention.

Having described the invention, what is claimed as new in support of Letters Patent is as follows:

1. A massage device for the human body comprising a jacket having a handgrip and a chamber in said jaceket having an electric heater, said heater comprising a heat absorbent core and a shaft on said core having an exposed heat delivering end, an applicator assembly for engagement with the body of the user and a connection between the applicator and the shaft, said applicator assembly comprising a permanent magnet, a heat transfer plate on a rear side of the applicator between said magnet and the connection, and a face plate on the forward side of the applicator, said face plate having a finish plate—constituting a body-engaging exterior surface.

2. A massage device for the human body as in claim 1 wherein said connection comprises screw threaded parts with one threaded part on the shaft and another complementarily threaded part on the applicator assembly.

3. A massage device for the human body as in claim 1 wherein the weight of the applicator assembly exceeds the weight of the jacket.

4. A massage device for the human body as in claim 1 wherein the weight of the applicator assembly is substantially twice the weight of the jacket.

5. A massage device for the human body as in claim 1 wherein the applicator assembly has an arcuate perimeter and the transverse dimension of the applicator assembly is in excess of thickness dimension of the applicator assembly.

6. A massage device for the human body as in claim 5 wherein the ratio of transverse dimension of the applicator assembly to thickness dimension of the applicator assembly is in excess of two to one.

7. A massage device for the human body as in claim 5 wherein the permanent magnet is annular in shape and a portion of the mass of said heat transfer plate is lodged within a central opening of the magnet.

8. A massage device for the human body as in claim 5 wherein the permanent magnet is annular in shape, a portion of the mass of said heat transfer plate is lodged within a central opening of the magnet and said face plate is at the centralized location overlying the central opening of the magnet.

9. A massage device for the human body as in claim 8 wherein said heat transfer plate and said face plate are of paramagnetic material.

10. A massage device for the human body as in claim 8 wherein said permanent magnet, said heat transfer plate and said face plate are non-releasably joined together at mutually contacting areas.

11. A massage device for the human body as in claim 8 wherein the perimeter of said applicator assembly is arcuately bevelled on the side adjacent the face plate.

12. A massage device for the human body as in claim 8 wherein said finish plate is made of non-magnetic material affixed to the applicator assembly at a location surmounting said face plate.

13. A massage device for the human body as in claim 8 wherein there is an annular ring around an exterior edge of the magnet.

* * * * *